(12) United States Patent
Elder

(10) Patent No.: US 8,239,582 B2
(45) Date of Patent: Aug. 7, 2012

(54) HAND-HELD TEST METER WITH DISRUPTION AVOIDANCE CIRCUITRY

(75) Inventor: David Elder, Inverness (GB)

(73) Assignee: Cilag GmbH International, Zug (CH)

( * ) Notice: Subject to any disclaimer, the term of this patent is extended or adjusted under 35 U.S.C. 154(b) by 116 days.

(21) Appl. No.: 12/824,473

(22) Filed: Jun. 28, 2010

(65) Prior Publication Data

US 2011/0296158 A1    Dec. 1, 2011

Related U.S. Application Data

(60) Provisional application No. 61/349,133, filed on May 27, 2010.

(51) Int. Cl.
*G06F 3/00* (2006.01)

(52) U.S. Cl. ............................... 710/2; 710/8

(58) Field of Classification Search .................. None
See application file for complete search history.

(56) References Cited

U.S. PATENT DOCUMENTS

| | | | |
|---|---|---|---|
| 5,708,247 A | 1/1998 | McAleer et al. | |
| 5,951,836 A | 9/1999 | McAleer et al. | |
| 6,241,862 B1 | 6/2001 | McAleer et al. | |
| 6,284,125 B1 | 9/2001 | Hodges et al. | |
| 6,413,410 B1 | 7/2002 | Hodges et al. | |
| 6,733,655 B1 | 5/2004 | Davies et al. | |
| 7,112,265 B1 | 9/2006 | McAleer et al. | |
| 7,149,891 B2 * | 12/2006 | Bruner et al. ................. | 713/100 |
| 7,241,265 B2 | 7/2007 | Cummings et al. | |
| 7,250,105 B1 | 7/2007 | Davies et al. | |
| 7,673,090 B2 | 3/2010 | Kaushik et al. | |
| 7,778,244 B1 * | 8/2010 | Sheikh et al. ................. | 370/363 |
| 2003/0225955 A1 | 12/2003 | Feldstein et al. | |
| 2006/0200813 A1 | 9/2006 | Young et al. | |
| 2007/0084734 A1 | 4/2007 | Roberts et al. | |
| 2007/0087397 A1 | 4/2007 | Kraft et al. | |
| 2008/0183909 A1 * | 7/2008 | Lim et al. ........................ | 710/14 |

(Continued)

FOREIGN PATENT DOCUMENTS

WO    WO 2010/049669 A1    5/2010

OTHER PUBLICATIONS

International PCT Search Report, PCT Application No. PCT/GB2011/000810, dated Oct. 18, 2011, 3 pages European Patent Office, Rijswijk, Netherlands.

*Primary Examiner* — Eron J Sorrell

(57) ABSTRACT

A hand-held test meter for use with an analytical test strip configured for the determination of an analyte in a bodily fluid sample includes a USB interface, a microcontroller block configured for boot strap loading (BSL) of data into the hand-held test meter via a serial signal and a circuit disruption avoidance block. The circuit disruption avoidance block includes a USB to serial bridge sub-block with (i) a USB input(s), (ii) a serial output(s) configured to provide a serial signal for BSL of data to the microcontroller block; and (iii) a plurality of general purpose input/outputs (GPIO). The circuit disruption avoidance block also includes a BSL enable gate/buffer sub-block. At least two of the GPIO are configured to provide BSL control signals to the microcontroller block via the BSL enable gate/buffer sub-block and the USB to serial bridge sub-block is configured to send the data to the microcontroller block via the at least one serial output.

14 Claims, 6 Drawing Sheets

U.S. PATENT DOCUMENTS

| | | |
|---|---|---|
| 2008/0288764 A1 | 11/2008 | Lu |
| 2009/0013229 A1 | 1/2009 | Taylor et al. |
| 2009/0076358 A1 | 3/2009 | Reggiardo et al. |
| 2009/0198770 A1 | 8/2009 | Jiang |
| 2010/0130183 A1 | 5/2010 | Kretz et al. |
| 2011/0054282 A1* | 3/2011 | Nekoomaram et al. ...... 600/347 |
| 2011/0213225 A1* | 9/2011 | Bernstein et al. ............ 600/309 |
| 2011/0289497 A1* | 11/2011 | Kiaie et al. ................... 717/171 |

* cited by examiner

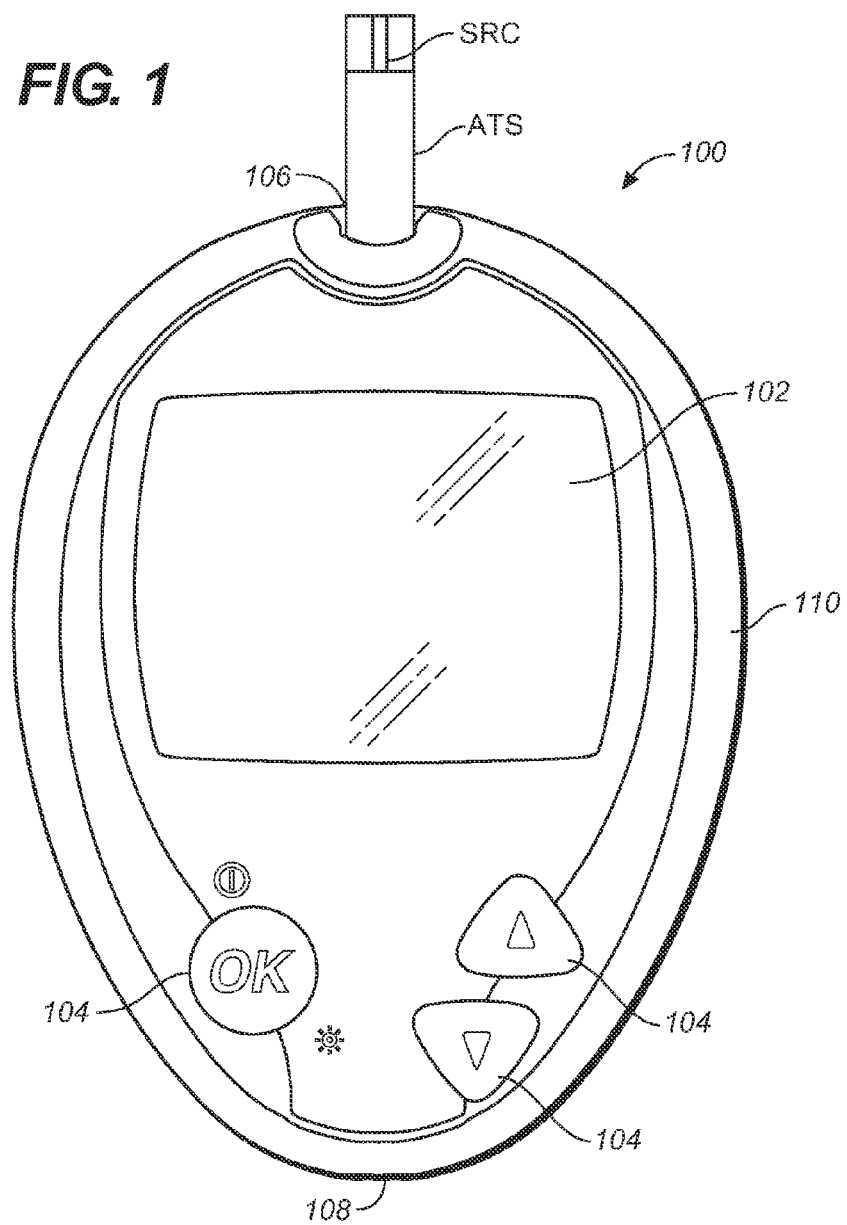
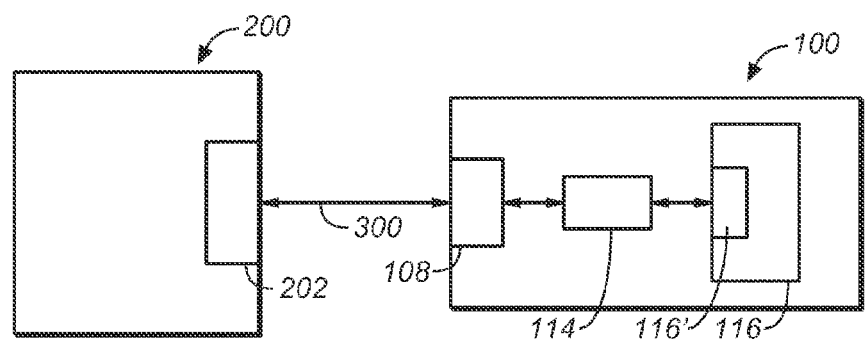

HAND-HELD TEST METER WITH DISRUPTION AVOIDANCE CIRCUITRY

BACKGROUND OF THE INVENTION

1. Field of the Invention

The present invention relates, in general, to medical devices and, in particular, to hand-held test meters, hand-held test meters in combination with peripheral devices, and related methods.

2. Description of Related Art

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using a hand-held test meter in combination with analytical test strips (e.g., electrochemical-based analytical test strips).

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which:

FIG. 1 is a simplified top view depiction of a hand-held test meter with a circuit disruption avoidance block according to an embodiment of the present invention interfaced with an analytical test strip;

FIG. 2 is a simplified block diagram of the hand-held test meter of FIG. 1 interfacing with a peripheral device such as, for example, a personal computer;

FIG. 4 is a diagram depicting the manner in which the partial simplified electrical schematic diagrams of FIGS. 4A, 4B, 4C and 4D are arranged to yield a simplified electrical schematic diagram depicting the integration of a USB interface, USB power detection circuitry block and a circuit disruption avoidance block of a hand-held test meter according to an embodiment of the present invention;

DETAILED DESCRIPTION OF ILLUSTRATIVE EMBODIMENTS

Figure 3:
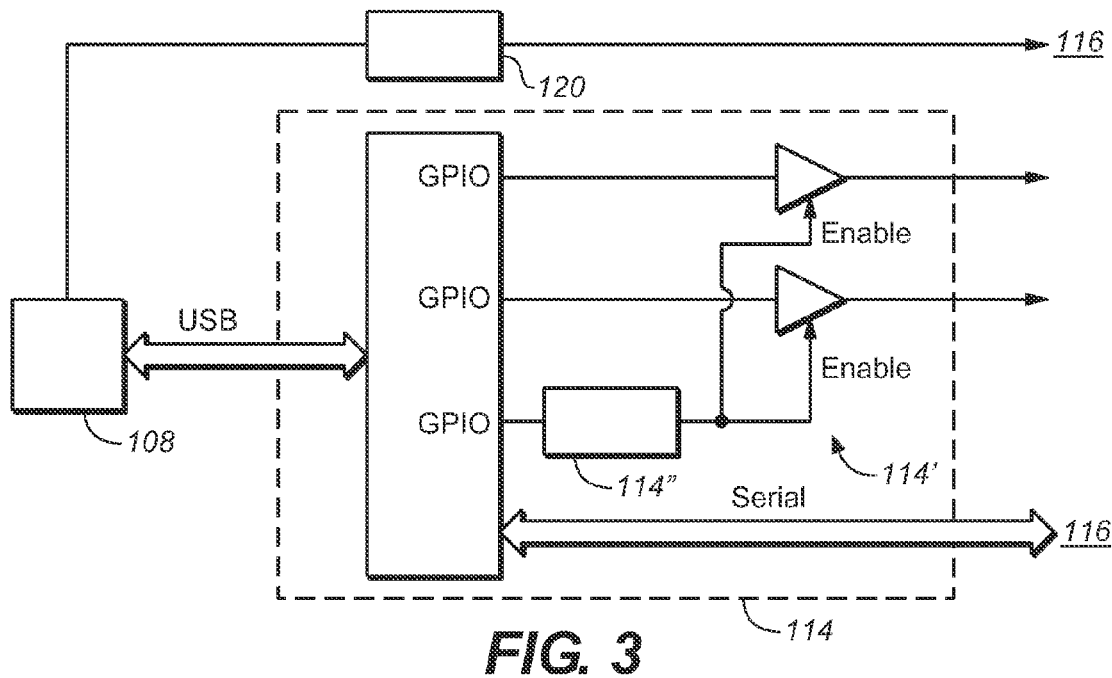
FIG. 3 is a simplified block diagram of various blocks of a hand-held test meter according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, hand-held test meters according to embodiments are configured for use with an analytical test strip in the determination of an analyte (such as glucose) in a bodily fluid sample (for example, a whole blood sample). Such hand-held test meters include a universal serial bus (USB) interface, a microcontroller block configured for boot strap loading (BSL) of data into the hand-held test meter via a serial signal, and a circuit disruption avoidance block (also referred to herein as disruption avoidance circuitry). The circuit disruption avoidance block includes at least (i) a USB to serial bridge sub-block with at least one USB input, at least one serial output configured to provide a serial signal for BSL of data to the microcontroller block; and a plurality of general purpose input/outputs (GPIO); and (ii) a BSL enable gate/buffer sub-block. In addition, at least two of the GPIO are configured to provide BSL control signals (such as, for example, RESET and TCK control signals) to the microcontroller block via the BSL enable gate/buffer sub-block and the USB to serial bridge sub-block is configured to send the BSL data to the microcontroller block via the at least one serial output. The BSL of operating software upgrade data onto hand-held test meters according to embodiments of the present invention can occur, for example, in 90 seconds or less while avoiding disruptions from spurious signals.

Hand-held test meters according to embodiments of the present invention are beneficial in that they provide for the extremely robust and quick BSL of data (such as downloading of encrypted or unencrypted operating software upgrades) into the hand-held test meter across a standard USB connection and for the robust operation of the hand-held test meter via avoidance of disruption caused by spurious signals emanating from the hand-held test meter's USB interface.

FIG. 1 is a simplified top view depiction of a hand-held test meter 100 with disruption avoidance circuitry according to an embodiment of the present invention interfaced with an analytical test strip ATS. Once one skilled in the art is apprised of the present disclosure, he will recognize that an example of a hand-held test meter that can be readily modified as a hand-hand test meter according to the present invention is the commercially available OneTouch® Ultra® 2 glucose meter from LifeScan Inc. (Milpitas, Calif.). Additional examples of hand-held test meters that can also be modified are found in U.S. Patent Application Publications No's. 2007/0084734 and 2007/0087397 and in PCT Patent Application PCT/GB2009/002502, each of which is hereby incorporated herein in full by reference.

Hand-held test meter 100 includes a display 102, user interface buttons 104, a strip port connector 106, a USB interface 108, and a housing 110. Display 102 can be, for example, a liquid crystal display or a bi-stable display configured to show a screen image. Examples of a screen image include a glucose concentration, a date and time, an error message and a user interface for instructing a user how to perform a test.

Strip port connector 106 is configured to operatively interface with analytical test strip ATS. Therefore, analytical test strip ATS is configured for operative insertion into strip port connector 106. Analytical test strip ATS can be any suitable analytical test strip including an electrochemical-based analytical test strip such as the commercially available One-Touch® Ultra® glucose test strip from LifeScan Inc. (Milpitas, Calif.). Examples of analytical test strips can be found in U.S. Pat. Nos. 5,708,247; 5,951,836; 6,241,862; 6,284,125; 6,413,410; 6,733,655; 7,112,265; 7,241,265; and 7,250,105, each of which is hereby incorporate herein in full by reference.

Once analytical test strip ATS is interfaced with hand-held test meter 100, or prior thereto, a bodily fluid sample (e.g., a whole blood sample) is dosed into a sample-receiving chamber SRC of analytical test strip ATS. Analytical test strip ATS can include enzymatic reagents that selectively and quantitatively transforms an analyte into another predetermined chemical form. For example, analytical test strip ATS can include an enzymatic reagent with ferricyanide and glucose oxidase so that glucose can be physically transformed into an oxidized form.

Hand-held test meter 100 further includes electronic circuitry within housing 110 such as a memory block (not shown), a microcontroller block (not shown in FIG. 1), a circuit disruption avoidance block (not shown in FIG. 1) and other electronic components (also not shown in FIG. 1) for applying a test voltage to analytical test strip ATS, and also for measuring an electrochemical response (e.g., plurality of test current values) and determining an analyte based on the electrochemical response. The memory block of hand-held test meter 100 includes a suitable algorithm that determines an analyte based on the electrochemical response of analytical test strip ATS. To simplify the current descriptions, the figures do not depict all such electronic circuitry.

FIG. 2 is a simplified block diagram of hand-held test meter 100 interfacing with (also referred to herein as being in combination with) a peripheral device 200 via a standard Universal Serial Bus (UBS) connector (cable) 300. Peripheral device 200 can be any suitable peripheral device including, for example, a personal computer (PC).

Peripheral device 200 includes a USB module 202 configured to transfer data from peripheral device 200 to hand-held test meter 100 via USB connector 300. Such a data transfer can include, for example, the transfer (download) of operating software for hand-held test meter 100 and upgrades to operating software for hand-held test meter 100.

Hand-held test meter 100 includes a USB interface 108, a circuit disruption avoidance block 114 and a microcontroller block 116 with bootstrap loading (BSL) sub-block 116' therein. BSL sub-block 116' provides for signals from USB interface 108 to bypass the majority of the electronic circuitry of the hand-held test meter (such as a memory block) within housing 110 and be transferred to microcontroller block 116. However, as is clear from FIG. 2 and the description below, the signals do not bypass circuit disruption avoidance block 114.

As is explained further with respect to FIGS. 3, 4, and 4A-4D, circuit disruption avoidance block 114 includes a BSL enable gate/buffer sub-block 114' with a time delay sub-block 114" and is configured to prevent disruption of hand-held test meter 100 functionality by spurious signals emanating from USB interface 108. Such spurious signals can be, for example, transient signals induced by the attachment and detachment of standard USB connector 300 (e.g., a fluttering 5V signal), inadvertent toggling signals transmitted across USB connector 300 from peripheral device 200 during operation of peripheral device 200, or general electrical noise on USB connector 300. In the absence of circuit disruption avoidance block 114, such spurious signals (such as a spurious 5V flutter signal) can result in the inadvertent and deleterious activation of BSL sub-block 116', annoying and time-consuming lock-up of hand-held test meter 100, and/or erroneous functioning of hand-held test meter 100 during use.

FIG. 3 is a simplified block diagram of selected blocks of hand-held test meter 100. FIGS. 4A-4D are simplified electrical schematic diagrams depicting the integration of a USB interface, USB power detection circuitry block and a circuit disruption avoidance block of hand-held test meter 100. One skilled in the art will recognize that in FIGS. 4A-4D the USB interface consists essentially of the component labeled USB-MINI-B and, optionally ESD protection component D403, the USB power detection circuitry consists essentially of the components labeled T402 and T401 and the circuit disruption avoidance block of the components labeled U402, U405A, U405B, R458 and C490. However, one skilled will also recognize that numerous other components (such as resistors, capacitors, ground connections and test points) are depicted in FIGS. 4A-4D to illustrate the operative integration of the various blocks and that, for simplicity, these other components have not been assigned to any particular block of the hand-held test meter.

Referring to FIGS. 1, 2, 3, 4 and 4A-4D, hand-held test meter 100 includes a test strip port connector 106 (see FIG. 1), a universal serial bus (USB) interface 108 (including the component labeled USB-MINI-B in FIG. 4C), a microcontroller block 116 configured for boot strap loading (BSL) of data into hand-held test meter 100 via a serial signal (see FIG. 2 and the labeled signals of FIG. 3), and a circuit disruption avoidance block 114.

Figure 4A:
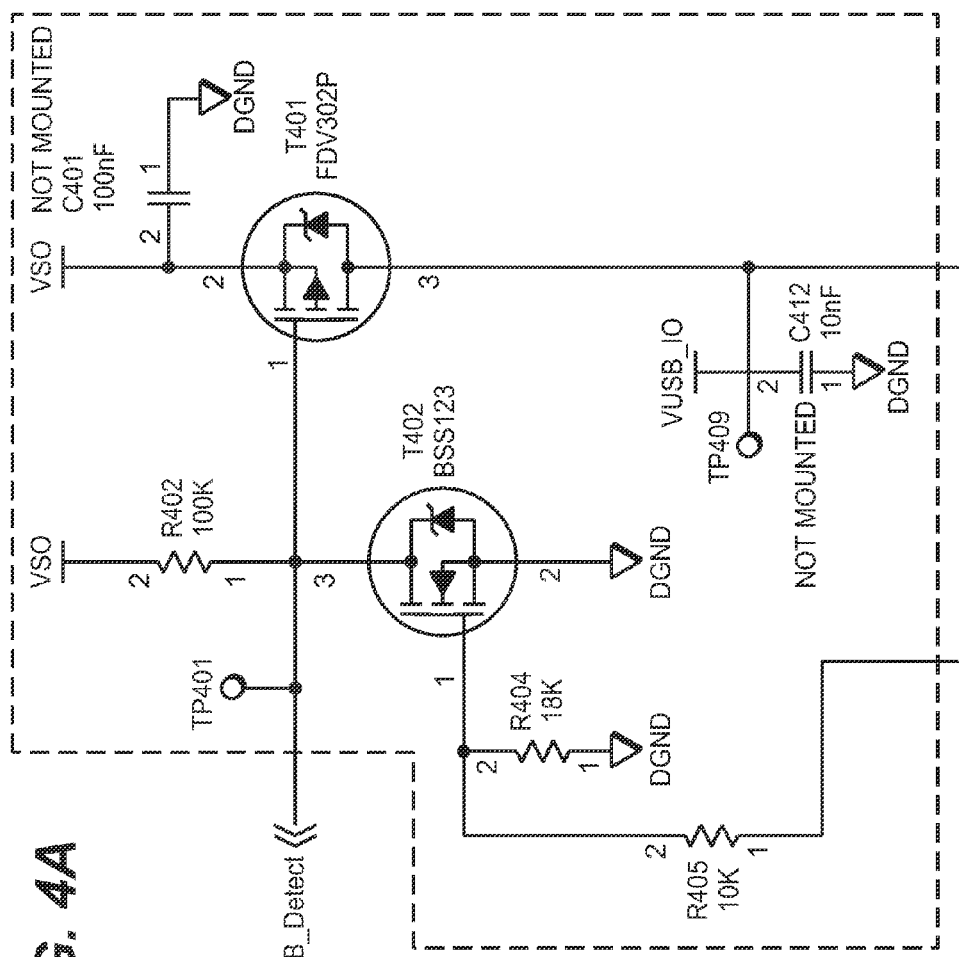
FIGS. 4A-4D are partial simplified electrical schematic diagrams that, when arranged as depicted by FIG. 4, yield a simplified electrical schematic diagram depicting the integration of a USB interface, USB power detection circuitry block and a circuit disruption avoidance block of a hand-held test meter according to an embodiment of the present invention.
Figure 4B:
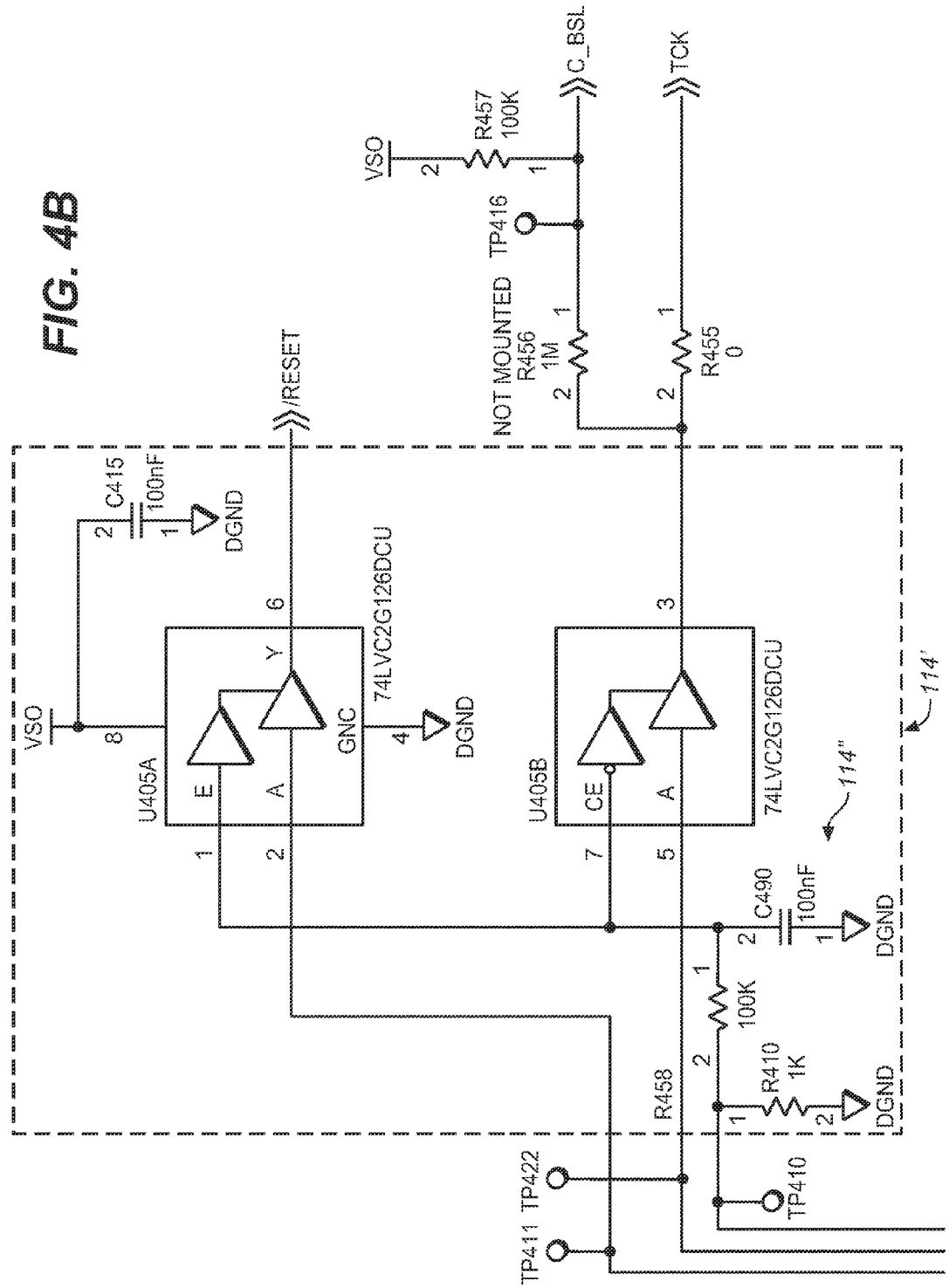
Figure 4C:
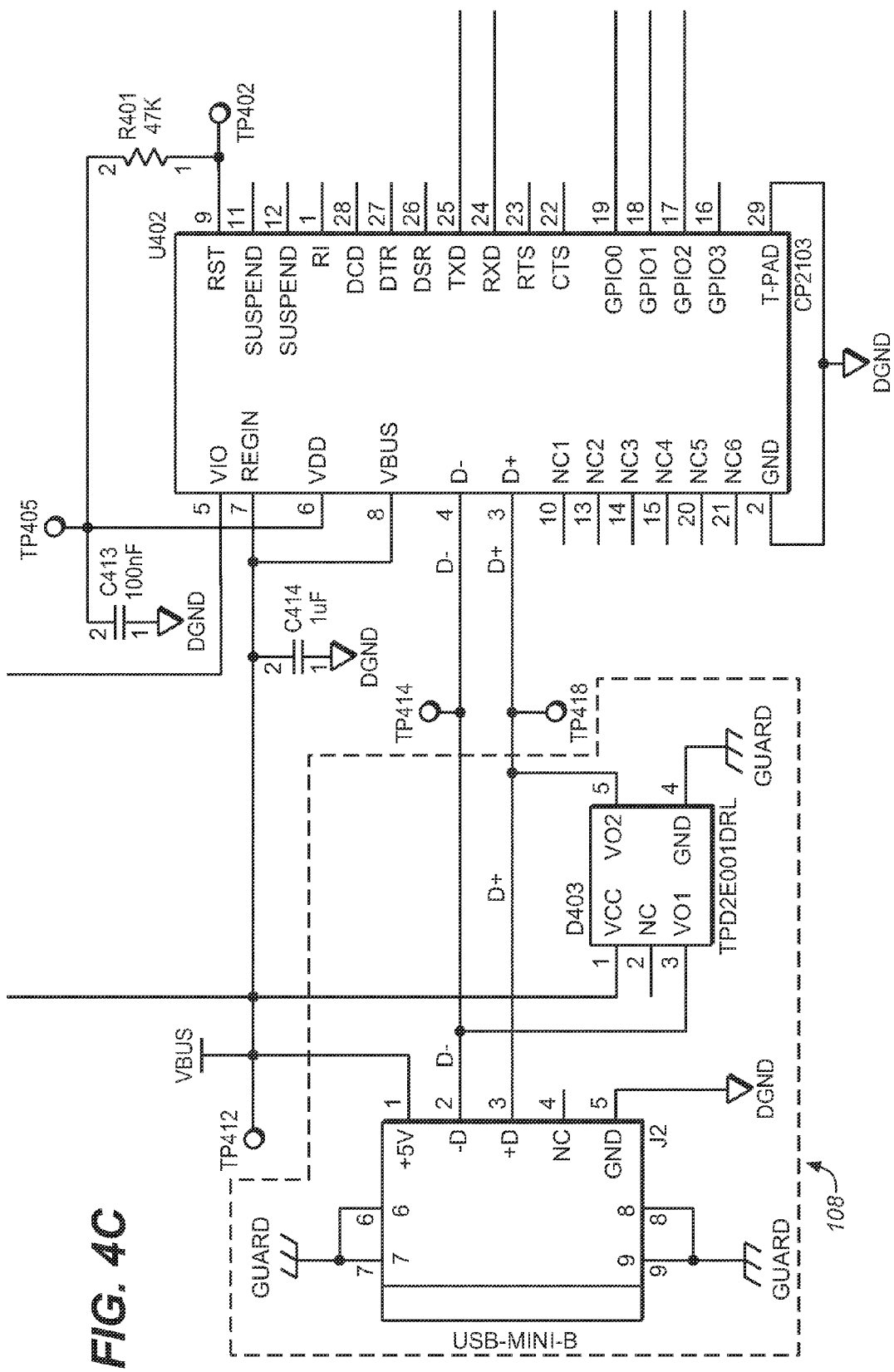
Figure 4D:
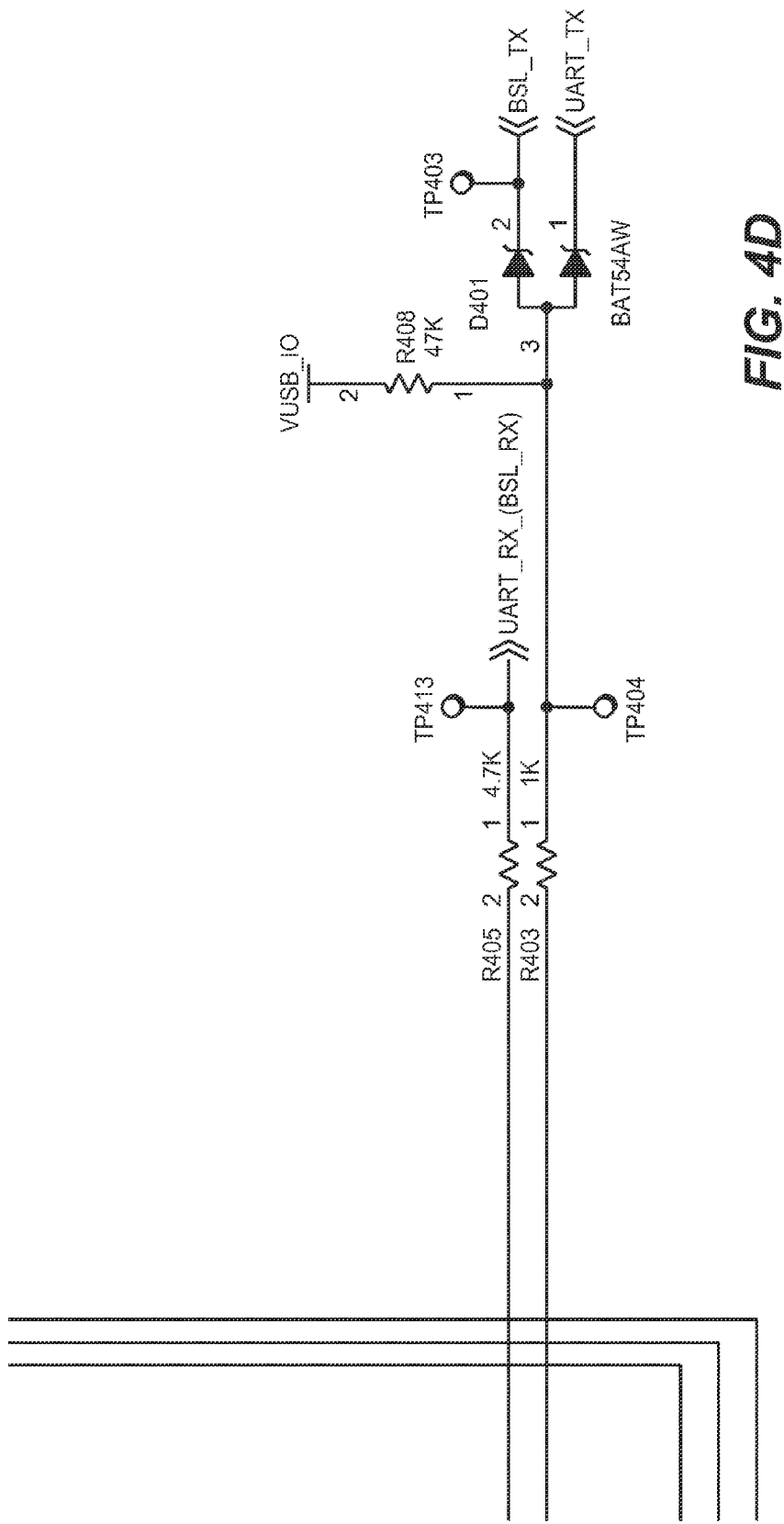

In the embodiment of FIGS. 4 and 4A-4D, USB interface 108 (depicted within the dashed lines of FIG. 4C) includes a commercial USB receptacle (e.g., USB Receptacle Part Number 67503-1020 available from Molex and labeled as USB-MINI-B in FIG. 4C) and an optional ESD protection component D403 (i.e., Texas Instruments part number TPD2E001 DRLR, an ESD SMD +/− 15 kV 2-Channel Low Capacitance Array). Moreover, USB interface 108 is configured to provide differential USB signals (labeled D− and D+) to component U402 of circuit disruption avoidance block 114 (see FIG. 4C in particular).

Microcontroller block 116 can be any suitable microcontroller block that is configured for BSL of data and operative control of hand-held test meter 100. A non-limiting example of such is a microcontroller block in the form of an MSP430 series microcontroller (commercially available from Texas Instruments, Texas, USA) configured to include a Texas Instruments BSL sub-block.

Circuit disruption avoidance block 114 includes: (i) at least a USB to serial bridge sub-block with at least one USB input; (ii) at least one serial output configured to provide a serial signal for BSL of data to the microcontroller block; and (iii) a plurality of general purpose input/outputs (GPIO). Such a USB to serial sub-block can be, for example, in the form of a CP2103 USB to Serial device integrated circuit (such as the component labeled U402 in FIG. 4C and labeled "USB to SERIAL Bridge" in FIG. 3) commercially available from Silicon Laboratories as an SMD single chip USB-2-UART Bridge, part number CP2103-GMR. This Silicon Laboratories device employs USB driver software (also available from Silicon Labs) for the conversion of standard USB protocol communication signals to standard RS232 serial communication signals (the standard USB protocol communication signals having been transferred from a peripheral device such as a PC). Once apprised of the present disclosure, one skilled in the art will recognize that the GPIO of the USB to serial bridge sub-block are configured to be driven and/or read by an application program residing in hand-held test meter 100 and/or controlled by programming within U402. In particular, U402 of FIG. 4C is configured to output standard TX (data transmit), DTR (data terminal ready) and RTS (ready to send) RS232 communication signals. U402 is also configured to handle additional standard RS232 signals such as RX (data receive), CTS (clear to send), DSR (data set ready), DCD (data carrier detect) and RI (ring indicator).

Circuit disruption avoidance block 114 also includes a BSL enable gate/buffer sub-block 114' (delineated by dashed lines in FIG. 4B). In the embodiment of FIGS. 4 and 4A-4D, BSL enable gate/buffer sub-block 114' includes the gates labeled U405A and U405B. Gates U405A and U405B are IC SMD dual bus buffer gates with 3-state outputs commercially available from Texas Instruments as part number SN74LVC2G126DCUR. However, any suitable gates may be employed in circuit disruption blocks included in embodiments of the present invention. U405A and U405B are essentially buffer gates that allow a signal to be routed or disconnected depending on the logic state of an enable signal.

Gates U405A and U405B provide the signals required to activate BSL sub-block 116' of microcontroller 116. Such signals are provided to BSL, TCK and RESET lines for control of the BSL sub-block (see FIG. 4B in particular). Referring to FIGS. 4A-4D, the RESET line signal is controlled by GPIO0 and the C_BSL and TCK line signals are controlled by GPIO1. Manipulation of GPIO0 and GPIO1 enables microcontroller block 116 to be put into bootstrap mode via signals from USB interface 108. GPIO2 is configured to provide a gating signal (also referred to as an enable signal) to BSL enable gate/buffer sub-block 114' that prevents noise on GPIO0 and GPIO1 from inadvertently triggering activation of the BSL mode. GPIO2 connects to the enable lines of U405A and U405B (see FIG. 4B in particular).

Therefore, circuit disruption avoidance block 114 includes at least two GPIO that are configured to provide BSL control signals to the microcontroller block via BSL enable gate/buffer sub-block 114' (see FIG. 3 and FIG. 4C where such GPIO are labeled GPIO0 and GPIO1). In addition, the USB to serial bridge sub-block (U402 in FIG. 4C) is configured to send the data to microcontroller block 116 via the at least one serial output for BSL of such data. Such serial output is labeled as "Serial" in FIG. 3 and as depicted as the output of the TXD and RXD pins of U402 in, for example, FIG. 4C.

In embodiments of the present invention, including the embodiment depicted in FIGS. 2, 3, 4 and 4A-4D, the GPIO cannot be toggled or otherwise manipulated by a peripheral device (such as a PC) connected to USB Interface 108 since GPIO functionality is not part of standard USB protocols (such as RS232-based protocols). Therefore, any spurious signals emanating from USB interface 108 are not propagated onto BSL control lines and do not cause deleterious disruption of the hand-held test meter's functionality. In other words, if BSL control lines (e.g., C_BSL and/or TCK and/or RESET) had been connected to RS232 handshake signals of the USB to serial bridge sub-block, then under some signaling conditions these lines could toggle creating the possibility of hand-held test meter 100 inadvertently entering BSL mode. However, this potential problem is resolved in embodiments of the present invention by employing GPIO outputs (which are unaffected by any serial communications, such as RS232 communication) to drive BSL control lines.

BSL enable gate/buffer sub-block 114' also includes a time delay sub-block 114" (see FIGS. 3 and 4B). Time delay sub-block 114" includes the circuit elements labeled R458 and C490 in FIG. 4B and is configured to provide an electrical time constant that prevents jitter from being propagated through the circuit disruption avoidance block to microcontroller 116. Time delay sub-block 114' also serves as an inexpensive hardware-based filter that enables gates U405A and U405B, and thus the BSL, TCK and RESET lines, a predetermined time after power is applied to U402 (e.g., a 10 ms delay). Moreover, the time-delay sub-block is connected to GPIO2 of U402 and is configured to enable placing the BSL Control Lines into a secure and robust tri-state when they are not required for operation of hand-held test meter 100.

FIGS. 3, 4 and 4A-4D depict an embodiment of the present invention wherein the hand-held test meter includes a USB power detection circuitry block 120 (delineated by dashed lines in FIG. 4A) in electrical communication with the USB interface 108 and the microcontroller block 116. FIG. 4A depicts how USB power detection circuitry block 120 includes the circuit components labeled T401 and T402. T410 and T402 are configured to sense bus power coming into hand-held test meter 100 over USB interface 108 and then signal microcontroller block 116 that a USB cable (element 300 in FIG. 2) is connected. This signaling of microcontroller block 116 occurs via the signal labeled USB_Detect in FIG. 4A. The bus power also provides power for the USB to serial bridge sub-block.

In the embodiment of FIGS. 4A-4D, T401 is a MOSFET SMD P-Channel Digital FET commercially available from Fairchild as part number FDV302P and T402 is a MOSFET SMD N-Channel commercially available from NXP Semiconductors as part number BSS123.

Embodiments of the present invention also include a hand-held test meter according to the present invention in combination with a peripheral device such as, for example, a personal computer. Such an embodiment is represented generally in FIG. 2 and can incorporate any of the techniques, benefits and characteristics of hand-held test meters according to embodiments of the present invention and described herein.

Figure 5:
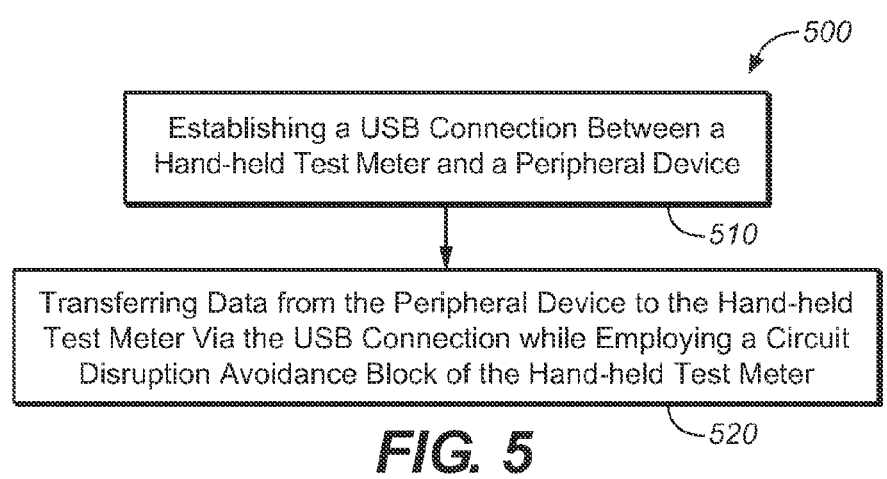
FIG. 5 is a flow diagram depicting stages in a method for operating a hand-held test meter according to an embodiment of the present invention.

FIG. 5 is a flow diagram depicting stages in a method 500 for operating a hand-held test meter according to an embodiment of the present invention and configured for the determination of an analyte (such as glucose) in a bodily fluid sample (e.g., a whole blood sample). Such a determination can involve determining the analyte in a bodily fluid sample that has been applied to an analyte test strip (e.g., an electrochemical-based analyte test strip).

Method 500 includes establishing a Universal Serial Bus (USB) connection between a hand-held test meter and a peripheral device (see step 510 of FIG. 5). At step 520 of method 500, data (for example, hand-held test meter operating software or upgrades to such operating software) is transferred from the peripheral device to the hand-held test meter via the USB connection while employing a circuit disruption avoidance block of the hand-held test meter to prevent USB connection related spurious signals from disrupting hand-held test meter functionality.

Once apprised of the present disclosure, one skilled in the art will recognize that method 500 can be readily modified to incorporate any of the techniques, benefits and characteristics of hand-held test meters according to embodiments of the present invention and described herein, as well as the combination of hand-held test meters and a peripheral device (such as a personal computer) described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A hand-held test meter for use with an analytical test strip in the determination of an analyte in a bodily fluid sample, the hand-held test meter comprising:
   a universal serial bus (USB) interface;
   a microcontroller block configured for boot strap loading (BSL) of data into the hand-held test meter via a serial signal; and
   a circuit disruption avoidance block that includes at least:
      a USB to serial bridge sub-block with
         at least one USB input;
         at least one serial output configured to provide a serial signal for BSL of data to the microcontroller block; and
         a plurality of general purpose input/outputs (GPIO); and
      a BSL enable gate/buffer sub-block;
   wherein at least two of the GPIO are configured to provide BSL control signals to the microcontroller block via the BSL enable gate/buffer sub-block;
   wherein the USB to serial bridge sub-block is configured to send the data to the microcontroller block via the at least one serial output; and
   wherein the circuit disruption avoidance block is configured to prevent USB connection related spurious signals from disrupting the hand-held meter functionality.

2. A hand-held test meter for use with an analytical test strip in the determination of an analyte in a bodily fluid sample, the hand-held test meter comprising:
   a universal serial bus (USB) interface;
   a microcontroller block configured for boot strap loading (BSL) of data into the hand-held test meter via a serial signal; and
   a circuit disruption avoidance block that includes at least:
      a USB to serial bridge sub-block with
         at least one USB input;
         at least one serial output configured to provide a serial signal for BSL of data to the microcontroller block; and
         a plurality of general purpose input/outputs (GPIO); and
      a BSL enable gate/buffer sub-block;
   wherein at least two of the GPIO are configured to provide BSL control signals to the microcontroller block via the BSL enable gate/buffer sub-block;
   wherein the USB to serial bridge sub-block is configured to send the data to the microcontroller block via the at least one serial output; and
   wherein the at least two GPIO are configured to be driven by programming residing within the hand-held test meter and to be unaffected by standard serial communications from the USB interface.

3. A method for operating a hand-held test meter configured for the determination of an analyte in a bodily fluid sample, the method comprising:
   establishing a Universal Serial Bus (USB) connection between a hand-held test meter and a peripheral device; and
   transferring data from the peripheral device to the hand-held test meter via the USB connection while employing a circuit disruption avoidance block of the hand-held test meter to prevent USB connection related spurious signals from disrupting hand-held test meter functionality.

4. The method of claim 3 further including:
   determining, following the transferring of data, an analyte in a bodily fluid sample using the hand-held test meter while employing the circuit disruption avoidance block to prevent USB connection spurious signals from disrupting the determination of the analyte.

5. The method of claim 3 wherein the peripheral device is a personal computer.

6. The method of claim 3 wherein the data is operating software for the hand-held test meter.

7. The method of claim 3 wherein the data is an update of operating software stored in the hand-held test meter.

8. The method of claim 3 wherein determining step includes determining an analyte in a bodily fluid sample applied to an analytical test strip.

9. The method of claim 3 wherein the circuit disruption avoidance block includes at least:
   a USB to serial bridge sub-block with
      at least one USB input;
      at least one serial output configured to provide a serial signal for BSL of data to the microcontroller block; and
      a plurality of general purpose input/outputs (GPIO); and
   a BSL enable gate/buffer sub-block;
   wherein at least two of the GPIO are configured to provide BSL control signals to the microcontroller block via the BSL enable gate/buffer sub-block; and
   wherein the USB to serial bridge sub-block is configured to send the data to the microcontroller block via the at least one serial output.

10. The method of claim 9 wherein the circuit disruption avoidance block further includes a time delay sub-block, and
    wherein at least one of GPIO is in electrical communication with the time delay sub-block such that a time delay is imposed on the BSL enable gate/buffer sub-block.

11. The method of claim 10 wherein the time delay sub-block is configured as a hardware filter.

12. The method of claim 9 wherein the at least two GPIO are configured to be driven by programming residing within the hand-held test meter and to be unaffected by standard serial communications from the USB interface.

13. A hand-held test meter in combination with a peripheral device, the hand-held meter comprising:
   a hand-held test meter with:
      a universal serial bus (USB) interface;
      a microcontroller block configured for boot strap loading (BSL) of data into the hand-held test meter via a serial signal; and
      a circuit disruption avoidance block that includes at least:
         a USB to serial bridge sub-block with
            at least one USB input;
            at least one serial output configured to provide a serial signal for BSL of data to the microcontroller block; and
            a plurality of general purpose input/outputs (GPIO); and
         a BSL enable gate/buffer sub-block; and
      a peripheral device,
   wherein at least two of the GPIO are configured to provide BSL control signals to the microcontroller block via the BSL enable gate/buffer sub-block,
   wherein the USB to serial bridge sub-block is configured to send the data to the microcontroller block via the at least one serial output, wherein the peripheral device is interfaced to the hand-held test meter via a USB connection; and wherein the circuit disruption avoidance block is configured to prevent USB connection related spurious signals from disrupting the hand-held meter functionality.

14. A hand-held test meter in combination with a peripheral device, the hand-held meter comprising:
- a hand-held test meter with:
  - a universal serial bus (USB) interface;
  - a microcontroller block configured for boot strap loading (BSL) of data into the hand-held test meter via a serial signal; and
  - a circuit disruption avoidance block that includes at least:
    - a USB to serial bridge sub-block with
      - at least one USB input;
      - at least one serial output configured to provide a serial signal for BSL of data to the microcontroller block; and
      - a plurality of general purpose input/outputs (GPIO); and
    - a BSL enable gate/buffer sub-block; and
- a peripheral device, wherein at least two of the GPIO are configured to provide BSL control signals to the microcontroller block via the BSL enable gate/buffer sub-block, wherein the USB to serial bridge sub-block is configured to send the data to the microcontroller block via the at least one serial output, wherein the peripheral device is interfaced to the hand-held test meter via a USB connection; and wherein the at least two GPIO are configured to be driven by programming residing within the hand-held test meter and to be unaffected by standard serial communications from the USB interface.

* * * * *